United States Patent
Montero Silva

(10) Patent No.: US 11,680,885 B2
(45) Date of Patent: Jun. 20, 2023

(54) METHOD, PROCESS, COMPOSITION AND KIT FOR MEASURING CONCENTRATION OF MOLECULES DISSOLVED IN THE CONTINUOUS PHASE OF A COLLOID

(71) Applicant: UNIVERSIDAD TÉCNICA FEDERICO SANTA MARÍA, Valparaíso (CL)

(72) Inventor: Francisco Montero Silva, Valparaíso (CL)

(73) Assignee: UNIVERSIDAD TÉCNICA FEDERICO SANTA MARÍA, Valparaíso (CL)

( * ) Notice: Subject to any disclaimer, the term of this patent is extended or adjusted under 35 U.S.C. 154(b) by 458 days.

(21) Appl. No.: 16/622,256

(22) PCT Filed: Jul. 27, 2018

(86) PCT No.: PCT/CL2018/050058
§ 371 (c)(1),
(2) Date: Dec. 12, 2019

(87) PCT Pub. No.: WO2019/023814
PCT Pub. Date: Feb. 7, 2019

(65) Prior Publication Data
US 2020/0103331 A1     Apr. 2, 2020

(30) Foreign Application Priority Data

Jul. 30, 2017  (CL) .................................. 1945-2017

(51) Int. Cl.
*G01N 15/04*     (2006.01)
*G01N 21/07*     (2006.01)
(Continued)

(52) U.S. Cl.
CPC ........... *G01N 15/042* (2013.01); *G01N 21/07* (2013.01); *B82Y 5/00* (2013.01); *G01N 2015/045* (2013.01); *G01N 2035/00495* (2013.01)

(58) Field of Classification Search
CPC ...... G01N 15/06; G01N 15/042; G01N 21/07; B01J 13/00; B01J 35/0013; B82Y 5/00
(Continued)

(56) References Cited

U.S. PATENT DOCUMENTS

| 2007/0042507 | A1 | 2/2007 | Tsang et al. |
| 2015/0024402 | A1 | 1/2015 | Roskamp et al. |
| 2021/0213438 | A1* | 7/2021 | Montero Silva ..... B01J 35/1033 |

FOREIGN PATENT DOCUMENTS

| CA | 2864614 A1 | 8/2013 |
| WO | 2005002544 A2 | 1/2005 |

OTHER PUBLICATIONS

International Search Report and Written Opinion for related International Application No. PCT/CL2018/050058, dated Nov. 27, 2018; English translation of ISR provided (14 pages).
(Continued)

*Primary Examiner* — Hoa Q Pham
(74) *Attorney, Agent, or Firm* — Procopio, Cory, Hargreaves & Savitch LLP

(57) ABSTRACT

A method for measuring a concentration of molecules, characterized in that the method measures the concentration of molecules dissolved in a continuous phase of a colloid and includes obtaining a test sample by mixing a number of molecules with a volume of colloid, obtaining a control sample by mixing a number of molecules with a volume of a composition comprising a particle-free solution extracted from a fraction of the continuous phase of same colloid used in the obtaining the test sample, so that a value of the concentration of molecules in the mixture is equal to the
(Continued)

value of the concentration of molecules in the test sample obtained in the obtaining the test sample, and submitting the test and the control samples obtained in the obtaining the test sample and obtaining the control sample to a process in order to concentrate the particles of the test sample.

1 Claim, 3 Drawing Sheets

(51) Int. Cl.
  *B82Y 5/00* (2011.01)
  *G01N 35/00* (2006.01)
(58) Field of Classification Search
  USPC ............ 356/432–440; 435/287.2, 288.7, 808
  See application file for complete search history.

(56) References Cited

OTHER PUBLICATIONS

Flores, Constanza. "Nanoparticulas de plata con potenciales aplicaciones en materiales implantables: sintesis, caracterización fisicoquimica y actividad bactericida" Doctoral Thesis in the Department of Chemistry, Universidad Nacional de La Plata; Mar. 28, 2014; 233 pages.

Exposito Harris, Ruth E. "Quitosanto, Un Biopolímero Con Aplicaciones en Sistemas De Liberación Controlada De Fármacos" Thesis of the Complutense University of Madrid, Feb. 12, 2010; 174 pages.

Molina, E. "Diseno y caracterizacion de nanoparticulas 4 constituidas porfarmacos triciclicos y polimeros solubles en agua estabilizadas par interacciones aromaticas" Thesis for Chemistry and Pharmaceuticals; 2016; 98 pages.

Bekdemir, A. et al. "A centrifugation-based physicochemical characterization method for the interaction between proteins and nanoparticles" Nature Communication, Oct. 20, 2016; 8 pages.

Dhar, S. et al., "Natural Gum Reduced/Stabilized Gold Nanoparticles for Drug Delivery Formulations," Chemistry. A European Journal. 2008; 14: 10244-10250 DOI: 10.1002/chem.200801093, 7 pages.

Bhumkar, D. et al., "Chitosan Reduced Gold Nanoparticles as Novel Carriers for Transmucosal Delivery of Insulin," Pharmaceutical Research Agosto—2007; vol. 24, No. 8, 1415-1426. DOI: 10.1007/s11095-007-9257-9, 12 pages.

Bobo, D. et al., "Nanoparticle-Based Medicines: A Review of FDA-Approved Materials and Clinical Trials to Date," Pharm. Res., 2016, 33, (10), pp. 2373-2387, 15 pages.

Ragelle, H. et al., "Nanoparticle-based drug delivery systems: a commercial and regulatory outlook as the field matures," Expert Opinion on Drug Delivery, 2017, vol. 14, No. 7, pp. 851 864, DOI: 10.1080/17425247.2016.1244187, 15 pages.

\* cited by examiner

METHOD, PROCESS, COMPOSITION AND KIT FOR MEASURING CONCENTRATION OF MOLECULES DISSOLVED IN THE CONTINUOUS PHASE OF A COLLOID

CROSS-REFERENCE TO RELATED APPLICATIONS

This application is a U.S. National Stage entry of PCT Application No: PCT/CL2018/050058 filed Jul. 27, 2018, which claims priority to Chilean Patent Application No. 1945-2017, filed Jul. 30, 2017, the contents of which are incorporated herein by reference.

FIELD OF APPLICATION

The present invention relates to the field of nanotechnology, more specifically to the evaluation of the interaction between particles of a colloid and molecules dissolved in the same colloid, even more specifically to a process, a composition, a kit, and a method for measuring the concentration of molecules dissolved in the continuous phase of a colloid.

BACKGROUND OF THE INVENTION

Colloids are systems in which particles, having at least one dimension between 1 and 1,000 [nm], are dispersed in a continuous phase of a composition other than particle composition (IUPAC).

Colloids have various industrial applications, for example, currently in the development of new pharmacological forms the use of colloids for the development of biomedical applications is promoted. Colloids are considered as a stable alternative of dispersion of molecules that can be applied in a specific tissue, which provide a sustained release of a molecule of interest, for example, a cytotoxic drug in a tumor, an analgesic or other. In order to advance in this delicate field of application, it is necessary to know the interaction between the particles of the colloid, and molecules dissolved in the same colloid.

The particles of a colloid may be metal particles, such as gold, silver, copper, iron, nickel or cobalt particles, which may or may not have an ionic charge. Additionally, these particles may be functionalized, for example, with mercaptoalkanoic acid molecules. The particles of a colloid may also be non-metallic particles, as in the case of dendrimers, liposomes, protein dispersions, and nucleic acid dispersions.

The molecules dissolved in a colloid establish reversible interactions with the components of the colloid, that is, the continuous phase and the dispersed particles of the colloid. With reversible interactions, equilibrium constants can be measured, thus evaluating the interaction between dispersed particles and molecules dissolved in the same colloid.

During the reversible interaction of molecules with particles of a colloid, two populations of molecules are generated. A population of molecules that interacts with the particles of the colloid, while another population of the molecules remains dissolved in the continuous phase of the colloid. This reversible interaction can be mediated by different phenomena, such as liophobia of dissolved molecules, Coulombic forces of attraction or repulsion between particles and dissolved molecules, among others.

The reversible interaction between dispersed particles and molecules dissolved in the colloid can be described by the reaction:

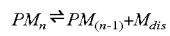

$$PM_n \rightleftharpoons PM_{(n-1)} + M_{dis}$$

where $PM_n$ represents the complex formed between the particles of a colloid and molecules that interact with the particles of the colloid, and where $M_{dis}$ represents the molecules dissolved in the continuous phase of the colloid.

In the state of the art, there are methods based on analytical ultracentrifugation techniques and localized surface plasmon (LSP) resonance spectrometry that allow to evaluate the interaction between particles of a colloid and molecules dissolved in the same colloid. For example, the study of the sedimentation pattern of gold nanospheres in the presence of albumin molecules by analytical ultracentrifugation coupled to LSPs resonance detection allowed to infer the number of protein molecules adsorbed onto metal nanospheres (Bekdemir and Stellacci, Nat Commun 7, 13121:28, 2016). Complex mathematical approaches indicated that, at equilibrium, a gold nanosphere can interact with 2 to 27 albumin molecules, depending on the size and chemical environment of the nanoparticle. In another example, the use of LSPs resonance spectrometry allowed to develop a method that optimizes the detection of interaction between metallic nanorods and peptide molecules (PharmaDiagnostics NV, Patent Application US20150024402, Jan. 22, 2015). In this case, the interaction was studied following changes in the wavelength of the maximum absorbance of the LSP resonance band of the nanorods after exposure of the particles to the peptides.

Although both methods can describe the interaction between peptide molecules and colloidal particles, they are based on techniques that limit interaction studies to restricted experimental conditions. For example, the use of analytical ultracentrifugation allows to determine changes in the sedimentation coefficient of particles, thus excluding from its analysis the study of interactions between particles of a colloid and molecules of low molecular mass. On the other hand, patent application US20150024402, which evaluates interactions by LSPs resonance spectrometry, limits its applications to the study of metal particles, excluding from its analysis the study of particulate systems without LSP, such as dendrimers, lipid particles, protein dispersions, emulsions, nucleic acid dispersions, synthetic polymer dispersions, etc.

According to scientific literature (Bobo, D., Robinson, K. J., Islam, J., Thurecht, K. J., Corrie, S. R.: Nanoparticle-Based Medicines: A Review of FDA-Approved Materials and Clinical Trials to Date, Pharm. Res., 2016, 33, (10), pp. 2373-2387; 2*Ragelle, H., Danhier, F., Préat, V., Langer, R., Anderson, D. G.: Nanoparticle-based drug delivery systems: a commercial and regulatory outlook as the field matures, Expert Opin. Drug Deliv., 2017, 14, (7), pp. 851-864), it is still necessary to have products and methods for measuring the concentration of different molecules dissolved in the continuous phase of colloids in order to understand the interaction established, for example, between drug molecules and colloidal particles, whose composition includes both metallic and non-metallic particles. The present invention provides a solution to these limitations of previous technologies.

SUMMARY DESCRIPTION OF THE INVENTION

The invention provides a process for obtaining a monophasic liquid composition equivalent to the continuous phase of a colloid. The composition must be extracted from a colloid and is used to obtain control samples during the execution of a method for measuring the concentration of molecules dissolved in the continuous phase of a colloid.

The invention also provides a monophasic liquid composition extracted from a colloid.

In addition, the invention also provides the components of a Kit. The Kit contains a volume of a colloid and a volume of a monophasic liquid composition extracted from a fraction of the same colloid, and which is equivalent to the continuous phase of the colloid. The Kit allows the user to measure the concentration of molecules of interest dissolved in the continuous phase of the colloid provided in the Kit. The concentration values of dissolved molecules obtained with the Kit components are used as reference values. The reference values allow the user to study in an accurate way the interaction between the molecules of interest (for example, drug molecules), and particles of other colloids also of interest.

Finally, the invention provides a method for measuring the concentration of molecules dissolved in the continuous phase of a colloid. To this end, the method comprises the obtention of a test sample and a control sample. The test sample contains molecules dissolved in a colloid, and the control sample contains molecules dissolved in a particle-free solution extracted from a fraction of the same colloid. To measure the concentration of molecules dissolved in the continuous phase of the colloid, a particle-free volume is obtained from the test sample. The concentration value of dissolved molecules in this volume is measured by comparison with the control sample.

Instructions are also provided so that the user can manipulate the Kit components. These instructions contain the information included in the method of the present invention.

DETAILED DESCRIPTION OF THE INVENTION

The present invention relates to a method for measuring the concentration of molecules dissolved in the continuous phase of a colloid, in addition to a process for obtaining a volume of particle-free solution from a volume of a colloid, a particle-free monophasic composition obtained from a volume of a colloid, and a kit for measuring the concentration of molecules of interest dissolved in the continuous phase of a colloid.

The present invention uses volumes of colloid with continuous phase that contain low concentration of residual compounds. This is because, during the synthesis and functionalization of the particles of a colloid, ions and residual molecules dissolved in the continuous phase of the colloid accumulate. These residual molecules interfere during interaction assays between the particles and the molecules of interest.

For example, the continuous phase of colloids of nanometric gold particles obtained by the trisodium citrate reduction method contains a high concentration of organic molecules derived from the incomplete oxidation of citrate ions and gold that was not incorporated into the structure of the nanometric particles. In addition, after functionalization of the nanometric particles with thiolated compounds, molecules not adsorbed to the surface of the particles also accumulate in the continuous phase of the colloid.

Figure 1:
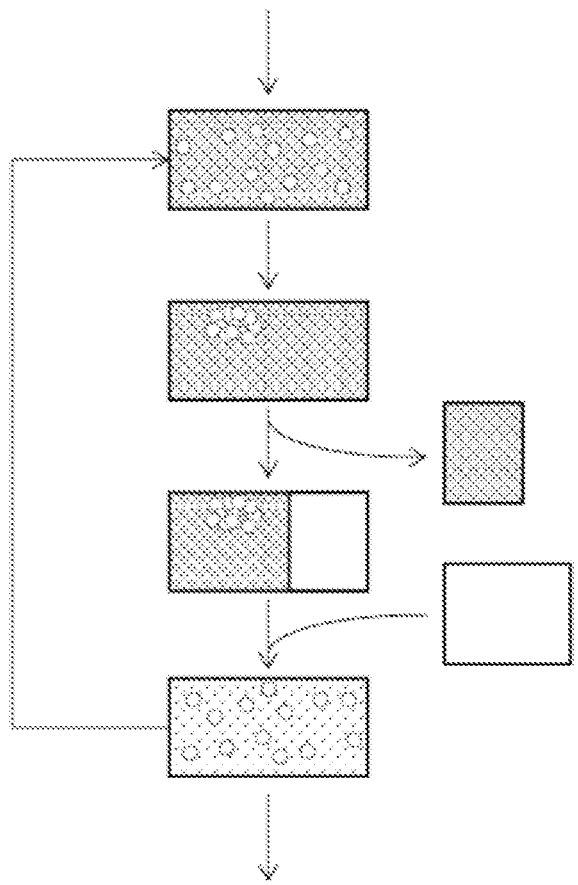
FIG. 1. Process scheme for obtaining volumes of a colloid with continuous phase containing low concentration of residual compounds.

Then, the process outlined in FIG. 1 is used to decrease the concentration of residual compounds in the continuous phase of colloids containing a high concentration of residual compounds. The process includes repetitive cycles of, a) concentrating the particles, b) discarding particle-free continuous phase and storing concentrated particles, and c) adding buffer volumes to the stored particles. As a condition, the buffer must keep the particles dispersed, avoiding flocculation or aggregation phenomena. The volumes of colloid thus obtained can be standardized taking as a reference a parameter proportional to the concentration of the dispersed particles. Fractions of colloid with continuous phase containing low concentration of residual compounds are used in concentration measurement assays of molecules dissolved in the continuous phase of the same colloid, or in other interaction assays.

As used in the present invention, the following terms should be understood as follows:

"Molecule" represents a defined chemical species.

"Particles" is considered equivalent to "dispersed particles", "particles of a colloid" and "particles contained in a colloid".

"Nanoparticle" is considered equivalent to particles with a diameter smaller than 150 [nm], equivalent to "dispersed nanoparticles", "nanoparticles of a colloid" and "nanoparticles contained in a colloid".

"Test sample" represents a volume of colloid that contains a defined number of dissolved molecules.

"Control sample" represents a volume of a solution extracted from a colloid also used to obtain a test sample, which does not contain detectable particles, and which contains a defined number of dissolved molecules.

"OD" means Optical Density and represents a parameter proportional to the concentration of nanoparticles in the colloid.

"g" means intensity of the Earth's gravitational field, whose value on the earth's surface is approximately 9.8 $[m/s^2]$.

"Particle-free solution" is understood as a monophasic liquid composition extracted from a colloid, and which is equivalent to the continuous phase of the same colloid.

All other terms used in the present invention should be interpreted in a manner similar to that set forth in the scientific literature. Furthermore, it is indicated that in the present invention the steps of the method and the process can operate in sequences other than those mentioned or illustrated in this description.

Figure 2:
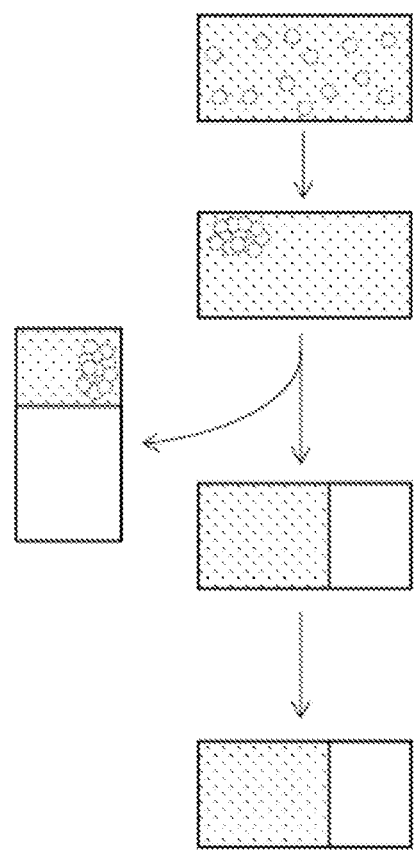
FIG. 2. Scheme of method for measuring the concentration of molecules dissolved in the continuous phase of a colloid.

The invention provides a method for measuring the concentration of molecules dissolved in the continuous phase of a colloid (FIG. 2). In general terms, the concentration of molecules dissolved in a fraction of the particle free colloid is measured. To evaluate this, in a first part the method obtains a test sample and a control sample. The test sample contains molecules dissolved in a colloid, and the control sample contains the same concentration of molecules dissolved in a particle-free solution extracted from the same colloid used to obtain the test sample. Under this design, the control sample is equivalent to a concentration of molecules dissolved in the continuous phase of the colloid, but does not include the effect of the interaction between molecules and particles. Subsequently, the samples are exposed to a condition that allows the particles of the test sample to be concentrated. After this process, if there is attractive interaction between the molecules and the particles, a portion of the test sample will be enriched in particles and molecules, while another majority portion will be free of particles and will contain a lower concentration of molecules. Then, a particle-free volume is recovered from the test sample. The fraction recovered is equivalent to the continuous phase of the colloid and includes the effect of the interaction between molecules and particles. Finally, the concentration of molecules dissolved in the continuous phase of the colloid is measured using equation 1:

$$[FC] = \frac{[\,]_0 \, @_{mp}}{@_{mc}}$$

where [FC] corresponds to the concentration of molecules dissolved in the continuous phase of a colloid, $[\,]_0$ corresponds to the value of the concentration of molecules used during the sampling steps, $@_{mp}$ corresponds to the empirical value of a parameter proportional to the number of molecules contained in a volume of particle-free test sample, and $@_{mc}$ corresponds to the empirical value of the same parameter proportional to the number of molecules contained in a volume of control sample. The concentration value obtained from this equation is equivalent to the concentration of molecules dissolved in the continuous phase of the colloid.

According to the above, the method for measuring the concentration of molecules dissolved in the continuous phase of a colloid comprises the steps of:

a) Obtaining a test sample by mixing a number of molecules with a volume of colloid;

b) Obtaining a control sample by mixing a number of molecules with a volume of particle-free solution extracted from a fraction of the same colloid used in step a), so that the value of the concentration of molecules in the mixture is equal to the value of the concentration of molecules in the test sample obtained in step a);

c) Submitting the samples obtained in steps a) and b) to a process in order to concentrate the particles of the test sample obtained in step a);

d) Recovering a particle-free volume from the test sample obtained in step c);

e) Recovering a volume from the control sample obtained in step c);

f) Measuring in the volume of the test sample recovered in step d) the value of a parameter proportional to the number of molecules contained in the sample volume;

g) Measuring in the volume of control sample recovered in step e) the value of the same parameter proportional to the number of molecules contained in the sample volume;

h) Measuring the concentration of molecules in the continuous phase of the colloid using the equation:

$$[FC] = \frac{[\,]_0 \, @_{mp}}{@_{mc}}$$

where [FC] corresponds to the concentration of molecules dissolved in the continuous phase of a colloid, $[\,]_0$ corresponds to the value of the concentration of molecules used during the sampling steps, $@_{mp}$ corresponds to the empirical value of a parameter proportional to the number of molecules contained in a volume of particle-free test sample obtained in step f), and $@_{mc}$ corresponds to the empirical value of the same parameter, but measured in the control sample obtained in step g).

The colloid comprises dispersions of particles chosen from: metal particles, metal oxides, silicates, dendrimers, liposomes, proteins, nucleic acids, polysaccharides, fulvic acids, humic acids, or synthetic polymers; specifically, the colloid comprises particles of gold, silver or copper, iron, nickel and cobalt, functionalized or not. More specifically, the colloid comprises nanometric particles of gold, silver or copper, iron, nickel and cobalt, functionalized with molecules containing a sulfhydryl functional group, or with molecules that have an amine functional group, or molecules with other functional groups that can react covalently with the surface of the particles.

On the other hand, in the method of the invention the dissolved molecules have a molecular mass between 50 [g/mol] and 200,000 [g/mol].

The steps of the method of the invention can be performed by any method available in the art, for example, step c) can be performed by centrifugation, ultrafiltration, or magnetization, depending on the physical and chemical characteristics of the dispersed particles and the continuous phase of the colloid.

Preferably, when using metal particles, if centrifugation is used, it is performed at between 20,000 and 30,000×g for a time between 5 to 30 [min]. For metallic and non-metallic particles, if ultrafiltration is used, the particles are concentrated in the retentate after exposure of the filter to an acceleration of 1,000 to 10,000×g, or exposure of the bottom of the filter to a pressure lower than atmospheric pressure. However, these parameters may vary depending on the sedimentation coefficient of the particles and the viscosity of the continuous phase. When the particles possess magnetic properties, they are concentrated by exposure to a magnet.

Finally, in step g) any available technique can be used to measure the number or concentration of dissolved molecules, such as: reversed-phase high-performance liquid chromatography and visible UV detection; reversed-phase high-performance liquid chromatography and infrared detection; liquid chromatography coupled to mass spectrometry; gas chromatography coupled to mass spectrometry; visible UV spectrophotometry and spectrofluorimetry.

Figure 3:
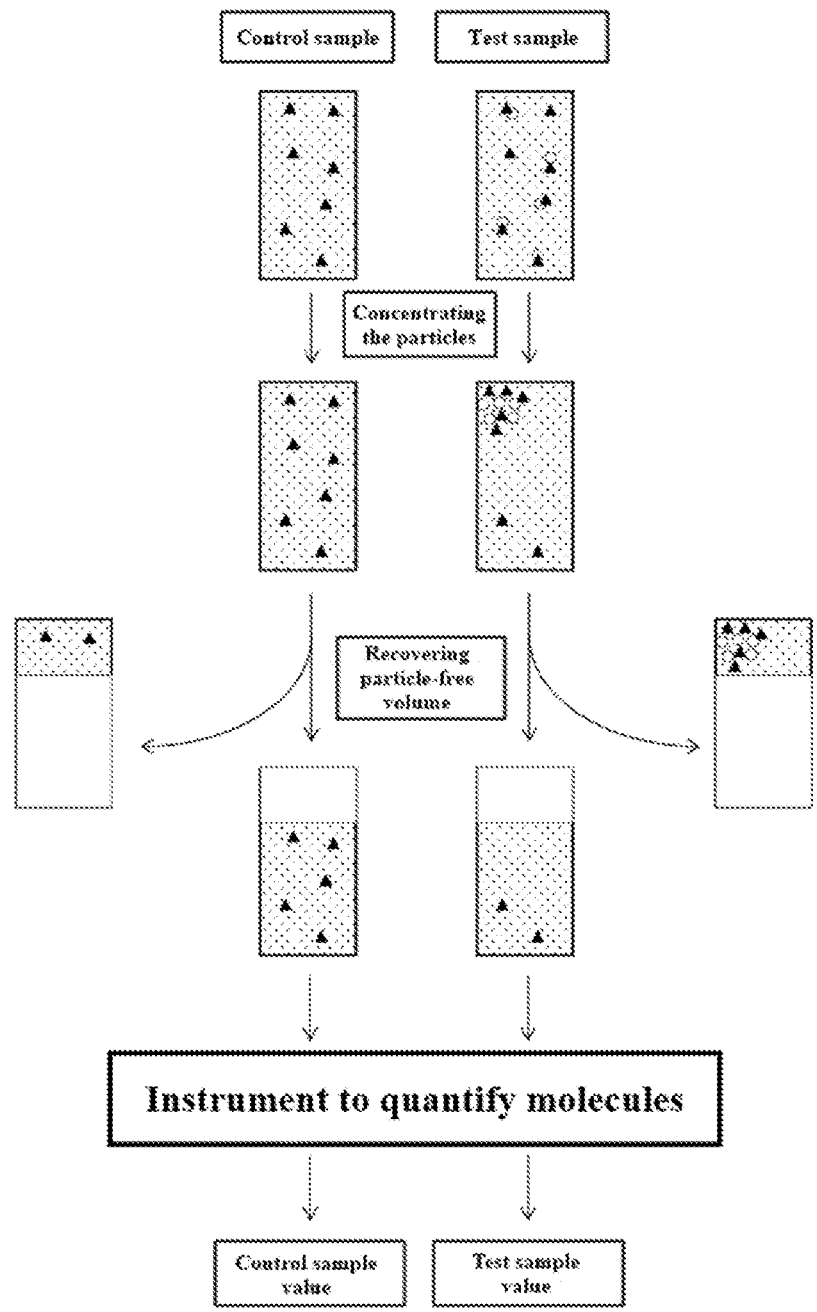
FIG. 3. Process scheme for obtaining a volume of particle-free solution extracted from a colloid.

In addition, the invention provides a process for obtaining a monophasic liquid composition from a volume of colloid. The composition, also provided in the kit, is free of particles and equivalent to the continuous phase of the colloid from which it was extracted. As shown in FIG. 3, the process for obtaining the volume of particle-free solution comprises the steps of a) concentrating the particles of a colloid sample, b) recovering a fraction of the particle-free sample, c) measuring in the recovered sample a parameter proportional to the concentration of particles of the colloid, and d) storing the particle-free continuous phase. Fractions of the volume of particle-free solution thus obtained can be used to obtain control samples. Control samples are used in measurement assays of concentration of molecules dissolved in the continuous phase of a colloid, or in other interaction assays.

The step of concentration of particles included in the process can be performed by any method available in the art, for example, step a) can be performed by centrifugation, ultrafiltration, or magnetization, depending on the physical and chemical characteristics of the dispersed particles and the continuous phase of the colloid.

Preferably, when using metal particles, if centrifugation is used, it is performed at between 20,000 to 30,000×g for a time between 5 to 30 [min]. For metallic and non-metallic particles, if ultrafiltration is used, the particles are concentrated in the retentate after exposure of the filter to an acceleration of 1,000 to 10,000×g, or exposure of the bottom of the filter to a pressure lower than atmospheric pressure. However, these parameters may vary depending on the sedimentation coefficient of the particles and the viscosity of the continuous phase. When the particles possess magnetic properties, they are concentrated by exposure to a magnet.

Finally, the invention provides a Kit that allows to measure the concentration of molecules of interest dissolved in the continuous phase of a colloid provided in the Kit. The Kit contains a volume of colloid and a volume of particle-free solution extracted from a fraction of the same colloid. The composition is obtained following the instructions of the process described previously.

For example, the Kit components can be obtained from colloids of gold nanometric particles functionalized with mercaptoalkanoic acid molecules. These colloids are stable and have been widely characterized in scientific literature. The stability of the colloid allows the storage and transport of the product for prolonged periods of time.

The use of the Kit components, following the instructions of the method set forth in the present invention, allows the laboratory user to obtain empirical concentration values of molecules of interest dissolved in the continuous phase of the colloid provided in the Kit. The concentration values of dissolved molecules obtained with the components of the Kit can be used as reference values. The reference values allow the user to accurately measure the concentration of molecules of interest dissolved in the continuous phase of other colloids of interest.

The invention can be better understood in the light of the examples detailed below, which are illustrative and not limiting thereof. In the context of these examples, Example 1 and Example 2 describe the composition of one of the possible forms that the components of the Kit in question can acquire, and Example 3 describes possible uses of the components of the Kit for measuring the concentration of different molecules dissolved in the continuous phase of the colloid obtained as described in example 1.

Example 1. Obtaining a Standard Colloid of Gold Nanoparticles Functionalized with 11-Mercaptoundecanoic Acid and with a Continuous Phase Containing Low Concentration of Residual Compounds (Standard AuNP@MUA Colloid)

To obtain a volume of AuNP@MUA colloid, gold nanoparticles with hydrodynamic diameter of 10 [nm] (50 [ml]) synthesized by citrate ion reduction were functionalized by exposure to a concentration of 11-mercaptoundenoic acid (MUA) of 100 [µM]. In order to decrease the concentration of residual compounds in the continuous phase of the colloid, the volume of functionalized nanoparticles was subjected to ultrafiltration by centrifugation using a commercial filter with exclusion size equal to 100 [kDa]. The sample was centrifuged at 4,000×g for 15 min and a 1 [ml] retentate enriched in nanoparticles was obtained. Permeate was discarded, and 9 [ml] of 1.2 [mM] sodium citrate buffer was added to the retentate. The ultrafiltration and resuspension process was repeated 6 times, obtaining a colloid rich in gold nanoparticles functionalized with MUA and with a continuous phase containing 1.2 [mM] sodium citrate, traces of gold, and a concentration of MUA equal or less to 1 [µM].

The functionalization of the nanoparticles with MUA molecules generates a hydrophobic layer of methylene groups located just above the surface of the metal core, and an outer layer containing negative electrical charges, because the carboxylic group of part of the 11-Mercaptoundenoic acid molecules remains deprotonated (zeta potential of the colloid equal to −33.5 [mV]).

Figure 4:
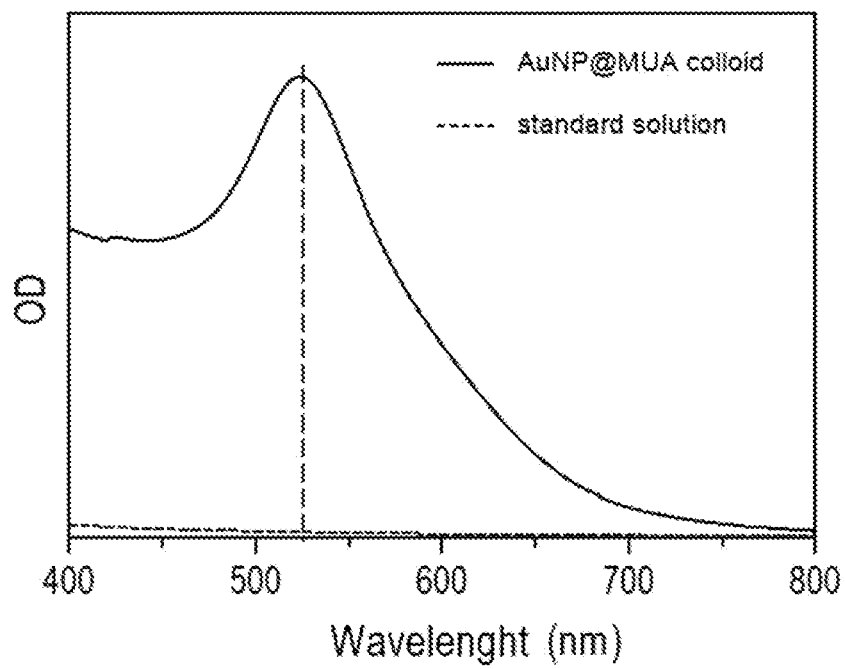
FIG. 4. Visible spectrum of standard AuNP@MUA colloid and standard particle-free solution extracted from a volume of the standard AuNP@MUA colloid.

The concentration of the AuNP@MUA particles contained in the colloid was standardized with respect to the optical density value of the maximum absorbance of the LSP band of the gold nanoparticles (OD maximum absorbance of the plasmon band=60/cm) (FIG. 4).

This colloid is used to obtain test samples during concentration measurement assays of molecules dissolved in the continuous phase of the standard AuNP@MUA colloid, and in other interaction assays.

Example 2. Obtaining a Standard Particle-Free Solution with a Composition Equivalent to the Continuous Phase of the Standard AuNP@MUA Colloid The standard AuNP@MUA colloid nanoparticles were concentrated by sedimentation. To this end, a volume of 1.5 [ml] of AuNP@MUA colloid was centrifuged at 24,000×g for 15 [min]. A volume of 1.4 [ml] of continuous phase free of AuNP@MUA nanoparticles was recovered and stored. As can be seen in FIG. 4, the volume of particle-free solution did not show an absorption band associated with the LSP of the gold nanoparticles, indicating that the particle-free solution obtained from the AuNP@MUA colloid does not contain detectable nanoparticles.

The concentration of AuNP@MUA particles contained in the particle-free solution was standardized with respect to the optical density value of the maximum absorbance of the LSP band of the gold nanoparticles (OD maximum absorbance of the plasmon band=0/cm).

This particle-free solution is used to obtain control samples during concentration measurement assays of molecules dissolved in the continuous phase of the standard AuNP@MUA colloid, and in other interaction assays. If necessary, it can also be used to dilute volumes of the standard AuNP@MUA colloid.

Example 3. Measurement of Concentration of Molecules Dissolved in the Continuous Phase of the Standard AuNP@MUA Colloid 3.1. Molecule: Methylene Blue.

The interaction between AuNP@MUA particles and methylene blue molecules was evaluated. To this end, the concentration of methylene blue molecules dissolved in the continuous phase of the standard AuNP@MUA colloid was measured.

To obtain the test sample, 140 [µl] of standard AuNP@MUA colloid obtained according to example 1 (OD maximum absorbance of the plasmon band=30/cm) were mixed with 5 [µl] of Milli-Q water and with 5 [µl] of a standard solution of methylene blue 60.00 [µM] dissolved in Milli-Q water. To obtain the control sample, 140 [µl] of standard solution obtained according to example 2 (OD maximum absorbance of the plasmon band=0/cm) were mixed with 5 [μl] of Milli-Q water and with 5 [μl] of a standard solution of methylene blue 60.00 [μM] dissolved in Milli-Q water. This results in a concentration of 2.00 [μM] of methylene blue in each sample.

Subsequently, in order to separate the continuous phase of the AuNP@MUA colloid particles, all samples were centrifuged at 24,000×g for 15 [min]. A volume of 130 [μl] free of nanoparticles was recovered from the test sample and control sample. In all volumes recovered, the amount of methylene blue was measured by reversed-phase high-performance liquid chromatography (RP-HPLC) and visible UV detection using a diode array detector. The methylene blue signal was detected at a wavelength of 665 [nm] (mAU). The amount of methylene blue was measured as the value of the signal integration area corresponding to the elution peak (mAU.min). Test samples (n=3) and control samples (n=3) were obtained and processed independently. Each sample was measured independently.

Figure 5:
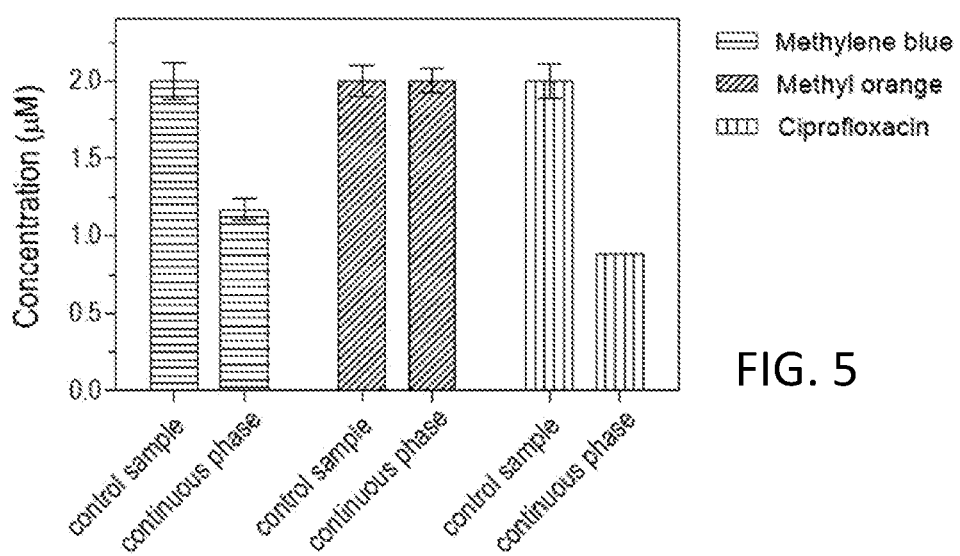
FIG. 5. Concentration of methylene blue, methyl orange and ciprofloxacin measured in the control samples and the continuous phase of the AuNP@MUA colloid.

The results of the concentration measurement indicated that, after incorporating 2.00 [μM] methylene blue into the colloid, the average concentration of methylene blue dissolved in the continuous phase of the AuNP@MUA colloid is 1.17 [μM], while in the control samples, equivalent to the continuous phase of the colloid, the concentration was 2.00 [μM] (FIG. 5).

3.2. Molecule: Methyl Orange.

Secondly, the interaction between AuNP@MUA particles and methyl orange molecules was evaluated. To this end, the concentration of dissolved methyl orange molecules in the continuous phase of the standard AuNP@MUA colloid was measured. For this, assays identical to those performed with methylene blue were performed, but using a standard solution of methyl orange 60.00 [μM] dissolved in Milli-Q water. This results in a concentration of 2.00 [μM] of methyl orange in each sample. The samples were further processed in the same manner as previously described in section 3.1 for methylene blue.

The amount of methyl orange was measured in all recovered volumes by RP-HPLC and visible UV detection using a diode array detector. The methyl orange signal was detected at a wavelength of 432 [nm] (mAU). The amount of methyl orange was measured as a value of the signal integration area corresponding to the elution peak (mAU.min). Test samples (n=3) and control samples (n=3) were obtained and processed independently. Each sample was measured independently.

The concentration measurement results indicated that, after incorporating methyl orange 2.00 [μM] into the colloid, the concentration of methyl orange molecules dissolved in the continuous phase of the standard AuNP@MUA colloid is 2.00 [μM]. The concentration of methyl orange in the control samples, equivalent to the continuous phase of the colloid, was also 2.00 [μM] (FIG. 5).

3.3 Molecule: Ciprofloxacin.

Thirdly, the interaction between AuNP@MUA particles and ciprofloxacin molecules was evaluated. To this end, the concentration of ciprofloxacin molecules dissolved in the continuous phase of the standard AuNP@MUA colloid was measured. For this, assays identical to those performed with methylene blue were performed, but using a standard solution of ciprofloxacin 60.00 [μM] dissolved in 50% methanol. This results in a concentration of 2.00 [μM] of ciprofloxacin in each sample. The samples were further processed in the same manner as previously described in section 3.1 for methylene blue.

In all recovered volumes, the amount of ciprofloxacin was measured by RP-HPLC and visible UV detection using a diode array detector. The ciprofloxacin signal was detected at a wavelength of 278 [nm] (mAU). The amount of ciprofloxacin was measured as value of the signal integration area corresponding to the elution peak (mAU.min). Test samples (n=3) and control samples (n=3) were obtained and processed independently. Each sample was measured independently.

The results of concentration measurement indicated that, after incorporating 2.00 ciprofloxacin [μM] into the colloid, the concentration of ciprofloxacin molecules dissolved in the continuous phase of the standard AuNP@MUA colloid is 0.88 [μM]. The concentration of ciprofloxacin in the control samples, equivalent to the continuous phase of the colloid, was 2.00 [μM] (FIG. 5).

The invention claimed is:

1. A method for measuring the concentration of molecules, characterized in that said method measures the concentration of molecules dissolved in the continuous phase of a colloid and comprises the steps of:
   a) obtaining a test sample by mixing a number of molecules with a volume of colloid;
   b) obtaining a control sample by mixing a number of molecules with a volume of a composition comprising a particle-free solution extracted from a fraction of the continuous phase of same colloid used in step a), so that a value of the concentration of molecules in the mixture is equal to the value of the concentration of molecules in the test sample obtained in step a);
   c) submitting the test and the control samples obtained in steps a) and b) to a process in order to concentrate the particles of the test sample obtained in step a);
   d) recovering a particle-free volume from the test sample obtained in step c);
   e) recovering a volume from the control sample obtained in step c);
   f) measuring in the particle-free volume recovered from the test sample in step d) the value of a parameter proportional to the number of molecules added in step a);
   g) measuring in the volume recovered from the control sample in step e) the value of the same parameter measured in step f); and
   h) measuring the concentration of molecules in the continuous phase of the colloid using the equation:

$$i)\ [FC] = \frac{[\ ]_0 @_{mp}}{@_{mc}}$$

wherein [FC] corresponds to the concentration of molecules dissolved in the continuous phase of a colloid, $[\ ]_0$ corresponds to the value of the concentration of molecules used in the steps a) and b), $@mp$ corresponds to an empirical value of the parameter proportional to the number of molecules contained in the particle-free volume recovered from the test sample obtained in step f), and $@_{mc}$ corresponds to an empirical value of the same parameter, but measured in the volume recovered from the control sample obtained in step g).

* * * * *